(12) United States Patent
Lim et al.

(10) Patent No.: US 9,198,585 B2
(45) Date of Patent: Dec. 1, 2015

(54) MOBILE TERMINAL AND METHOD OF MEASURING BIOELECTRIC SIGNALS THEREOF

(75) Inventors: Gukchan Lim, Seoul (KR); Sangmo Park, Seoul (KR); Seonghyok Kim, Seoul (KR); Seehyung Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 11 days.

(21) Appl. No.: 13/368,969

(22) Filed: Feb. 8, 2012

(65) Prior Publication Data

US 2013/0005310 A1 Jan. 3, 2013

(30) Foreign Application Priority Data

Jun. 29, 2011 (KR) .......................... 10-2011-0063728

(51) Int. Cl.
*A61B 5/024* (2006.01)
*A61B 5/0245* (2006.01)
*A61B 5/16* (2006.01)
*A61B 5/00* (2006.01)
*H04M 1/725* (2006.01)
*H04M 1/60* (2006.01)

(52) U.S. Cl.
CPC ........... *A61B 5/02438* (2013.01); *A61B 5/0245* (2013.01); *A61B 5/165* (2013.01); *A61B 5/6898* (2013.01); *H04M 1/72569* (2013.01); *H04M 1/6058* (2013.01)

(58) Field of Classification Search
CPC ..................... G06F 19/3475; H04N 21/42201; H04N 21/4325; H04N 21/4755; H04N 21/4826; A61B 5/0002; A61B 5/02438; A61B 5/0245; A61B 5/16; A61B 5/165; A61B 5/6887; A61B 5/6898

USPC ............. 455/550.1, 404.1, 414.1, 556.1, 401, 455/456.1, 456.3

See application file for complete search history.

(56) References Cited

U.S. PATENT DOCUMENTS

| | | | |
|---|---|---|---|
| 7,769,435 B2* | 8/2010 | Kuo et al. | 600/509 |
| 7,788,104 B2* | 8/2010 | Matsuo et al. | 704/276 |
| 7,874,983 B2* | 1/2011 | Zancho et al. | 600/300 |
| 2004/0147814 A1* | 7/2004 | Zancho et al. | 600/300 |
| 2005/0239493 A1* | 10/2005 | Batkin et al. | 455/550.1 |
| 2006/0061468 A1 | 3/2006 | Ruha | |
| 2006/0166702 A1 | 7/2006 | Dietz et al. | |
| 2010/0011388 A1* | 1/2010 | Bull et al. | 725/9 |

(Continued)

FOREIGN PATENT DOCUMENTS

| | | |
|---|---|---|
| CA | 2 428 250 | 11/2003 |
| JP | 2003-153905 | 5/2003 |

(Continued)

OTHER PUBLICATIONS

Ramesh Natarajan, "How to Send SMS Using Email to Majior US Cellphone Carriers", Aug. 20, 2010, www.thegeekstuff.com.*

(Continued)

*Primary Examiner* — Marcos Torres
*Assistant Examiner* — Hung Du
(74) *Attorney, Agent, or Firm* — KED & Associates LLP

(57) ABSTRACT

A mobile terminal and a method of measuring a bioelectric signal thereof are provided. When the mobile terminal enters a call mode, a user's pulse wave data are acquired using a plurality of electrodes provided in a body of the mobile terminal or a body of an earphone.

12 Claims, 10 Drawing Sheets

(56) References Cited

U.S. PATENT DOCUMENTS

2010/0123588 A1    5/2010   Cruz Hernandez
2010/0137027 A1*   6/2010   Kim ........................... 455/556.1
2011/0289454 A1*  11/2011   Houllier et al. ............... 715/810
2011/0294525 A1*  12/2011   Jonsson ........................ 455/466
2012/0172085 A1*   7/2012   Vuppu et al. ............... 455/556.1
2012/0303638 A1*  11/2012   Bousamra et al. ............ 707/751

FOREIGN PATENT DOCUMENTS

JP    2005-244375         9/2005
JP    2010200184  A  *    9/2010

OTHER PUBLICATIONS

European Search Report dated Oct. 25, 2012 for Application 12001114.3.

* cited by examiner

MOBILE TERMINAL AND METHOD OF MEASURING BIOELECTRIC SIGNALS THEREOF

CROSS-REFERENCE TO RELATED APPLICATION

This application claims benefit and priority from Korean Patent Application No. 10-2011-0063728, filed Jun. 29, 2011, the contents of which are hereby incorporated by reference in their entirety.

BACKGROUND

1. Field

Embodiments may relate to a mobile terminal and a method for measuring bioelectric signal thereof.

2. Background

Terminals can be divided into mobile terminals and stationary terminals. The mobile terminals can be classified as handheld terminals or vehicle mounted terminals according to whether users can personally carry the terminals.

In view of various types of services that are provided by mobile terminals, an improvement in the structure and/or software of mobile terminals is considered.

SUMMARY

An aspect of the present invention is to provide a mobile terminal and a method of measuring a bioelectric signal thereof that can sense a user's pulse wave.

In an aspect, a mobile terminal includes: a pulse wave sensing unit for acquiring a pulse wave signal using a plurality of electrodes and performing and outputting a signal processing of the acquired pulse wave signal; and a controller for controlling conversion to a call mode and acquiring pulse wave data using a pulse wave signal output from the pulse wave sensing unit in a state of operating in the call mode.

In another aspect, a method of measuring a bioelectric signal of a mobile terminal, the method includes: acquiring, if the mobile terminal enters a call mode, a user's pulse wave data using a plurality of electrodes contacting with the user's skin surface; acquiring an excited degree of the user based on the acquired pulse wave data; and terminating, if the excited degree is equal to or larger than a preset level, a call or outputting alarm for warning that the user is in an excited state.

BRIEF DESCRIPTION OF THE DRAWINGS

The accompanying drawings, which are included to provide a further understanding of described embodiments of the present invention and are incorporated in and constitute a part of this specification, illustrate embodiments of the present invention and together with the description serve to explain aspects and features of the present invention.

DETAILED DESCRIPTION

Embodiments of the present invention will now be described more fully with reference to the accompanying drawings, in which certain embodiments of the invention are illustrated. The invention may, however, be embodied in many different forms and should not be construed as being limited to the embodiments set forth herein; rather, these embodiments are described and/or illustrated so that this disclosure will be more thorough and complete, and will more fully convey the aspects of the invention to those skilled in the art.

Hereinafter, a mobile terminal according to embodiments of the present invention will be described below in more detail with reference to the accompanying drawings. In the following description, the suffixes "module" and "unit" are used in reference to components of the mobile terminal for convenience of description and do not have meanings or functions different from each other.

The mobile terminals described herein may include a cellular phone, a smart phone, a laptop computer, a digital broadcasting terminal, a personal digital assistant (PDA), a portable multimedia player (PMP), and a navigation system.

Figure 1:
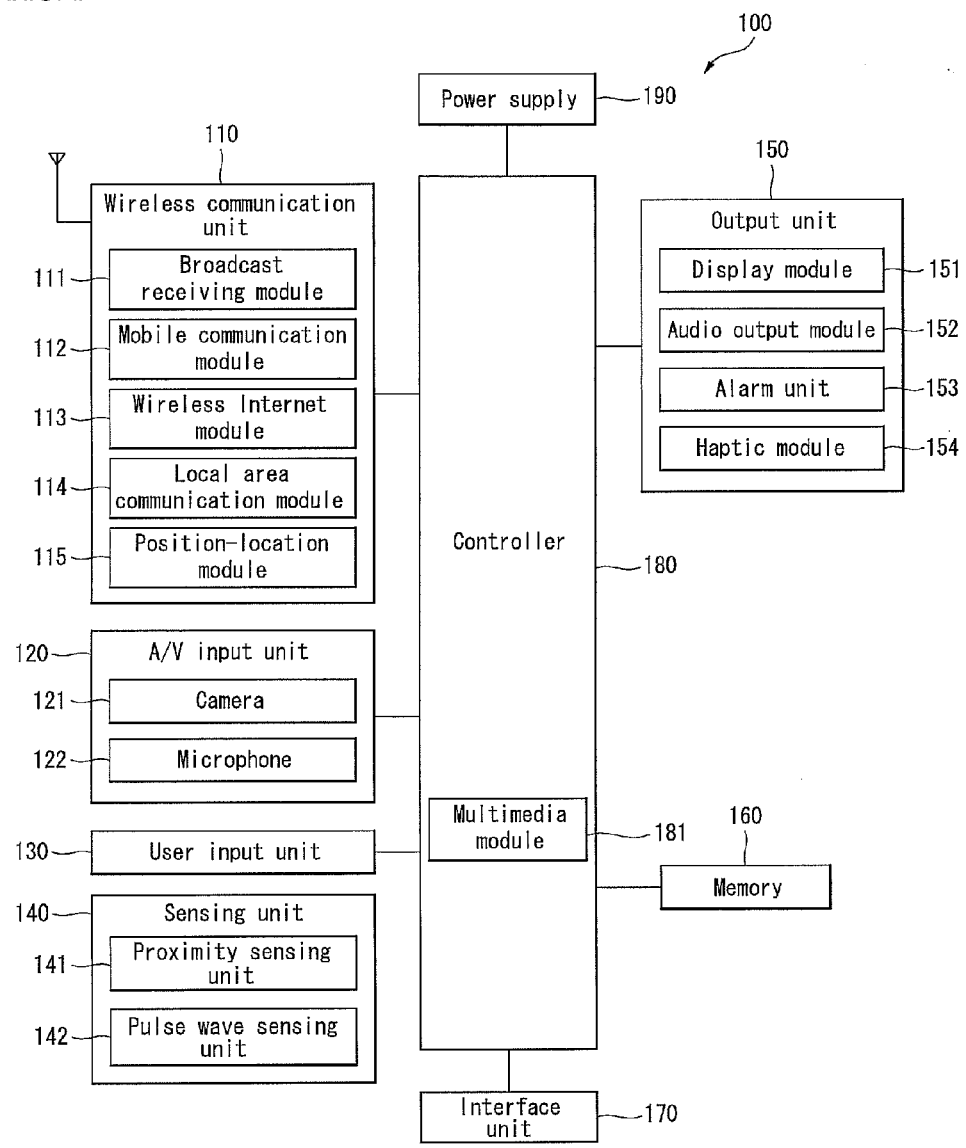
FIG. 1 is a block diagram illustrating a configuration of a mobile terminal according to embodiments of the present invention.

FIG. 1 is a block diagram of a mobile terminal 100 according to an embodiment of the present invention. It is understood that other embodiments, configurations and arrangements may also be provided. With reference to FIG. 1, the mobile terminal 100 may include a radio communication unit 110, an audio/video (A/V) input unit 120, a user input unit 130, a sensing unit 140, an output unit 150, a memory 160, an interface unit 170, a controller 180, and a power supply 190. Not all of the components shown in FIG. 1 are essential, and the number of components included in the mobile terminal 100 may be varied. The components of the mobile terminal 100, as illustrated with reference to FIG. 1 will now be described.

The radio communication unit 110 may include at least one module that enables wireless communication between the mobile terminal 100 and a wireless communication system or between the mobile terminal 100 and a network in which the mobile terminal 100 is located. For example, the radio communication unit 110 may include a broadcast receiving module 111, a mobile communication module 112, a wireless Internet module 113, a local area (or short-range) communication module 114, and a location information module 115.

The broadcast receiving module 111 may receive broadcasting signals and/or broadcasting related information from an external broadcasting management server through a broadcasting channel. The broadcasting channel may include a satellite channel and a terrestrial channel, and the broadcasting management server may be a server that generates and transmits broadcasting signals and/or broadcasting related information or a server that receives previously created broadcasting signals and/or broadcasting related information and transmits the broadcasting signals and/or broadcasting related information to a terminal.

The broadcasting signals may include not only TV broadcasting signals, wireless broadcasting signals, and data broadcasting signals, but also signals in the form of a combination of a TV broadcasting signal and a radio broadcasting signal. The broadcasting related information may be information on a broadcasting channel, a broadcasting program or a broadcasting service provider, and may be provided even through a mobile communication network. In the latter case, the broadcasting related information may be received by the mobile communication module 112.

The broadcasting related information may exist in any of various forms. For example, the broadcasting related information may exist in the form of an electronic program guide (EPG) of a digital multimedia broadcasting (DMB) system or in the form of an electronic service guide (ESG) of a digital video broadcast-handheld (DVB-H) system.

The broadcast receiving module 111 may receive broadcasting signals using various broadcasting systems. More particularly, the broadcast receiving module 111 may receive digital broadcasting signals using digital broadcasting systems such as a digital multimedia broadcasting-terrestrial (DMB-T) system, a digital multimedia broadcasting-satellite (DMB-S) system, a media forward link only (MediaFLO™) system, a DVB-H system, and an integrated services digital broadcast-terrestrial (ISDB-T) system. The broadcast receiving module 111 may receive signals from broadcasting systems providing broadcasting signals other than the above-described digital broadcasting systems.

The broadcasting signals and/or broadcasting related information received through the broadcast receiving module 111 may be stored in the memory 160. The mobile communication module 112 may transmit/receive a wireless signal to/from at least one of a base station, an external terminal and a server on a mobile communication network. The wireless signal may include a voice call signal, a video call signal or data in various forms according to the transmission and reception of text/multimedia messages.

The wireless Internet module 113 may correspond to a module for wireless Internet access and may be included in the mobile terminal 100 or may be externally attached to the mobile terminal 100. Wireless LAN (WLAN or Wi-Fi), wireless broadband (Wibro™), world interoperability for microwave access (Wimax™), high speed downlink packet access (HSDPA) and other technologies may be used as a wireless Internet technique.

The local area communication module 114 may correspond to a module for local area communication. Further, Bluetooth™, radio frequency identification (RFID), infrared data association (IrDA), ultra wideband (UWB) and/or ZigBee™ may be used as a local area communication technique.

The location information module 115 may confirm or obtain the position of the mobile terminal 100. The location information module 115 may obtain position information by using a global navigation satellite system (GNSS). The GNSS refers to a radio navigation satellite system that revolves around the earth and transmits reference signals to predetermined types of radio navigation receivers such that the radio navigation receivers may determine their positions on the earth's surface or near the earth's surface. The GNSS may include a global positioning system (GPS) of the United States, Galileo of Europe, a global orbiting navigational satellite system (GLONASS) of Russia, COMPASS of China, and a quasi-zenith satellite system (QZSS) of Japan among others.

A global positioning system (GPS) module is one example of the location information module 115. The GPS module 115 may calculate information regarding distances between one point or object and at least three satellites and information regarding a time when the distance information is measured and apply trigonometry to the obtained distance information to obtain three-dimensional position information on the point or object according to latitude, longitude and altitude at a predetermined time. A method of calculating position and time information using three satellites and correcting the calculated position and time information using another satellite may also be used. In addition, the GPS module 115 may continuously calculate the current position in real time and calculate velocity information using the location or position information.

As shown in FIG. 1, the A/V input unit 120 may input an audio signal or a video signal and include a camera 121 and a microphone 122. The camera 121 may process image frames of still images or moving pictures obtained by an image sensor in a video call mode or a photographing mode. The processed image frames may be displayed on a display module 151 which may be a touch screen.

The image frames processed by the camera 121 may be stored in the memory 160 or may be transmitted to an external device through the radio communication unit 110. The mobile terminal 100 may also include at least two cameras 121.

The microphone 122 may receive an external audio signal in a call mode, a recording mode or a speech recognition mode and process the received audio signal into electronic audio data. The audio data may then be converted into a form that may be transmitted to a mobile communication base station through the mobile communication module 112 and output in the call mode. The microphone 122 may employ various noise removal algorithms (or noise canceling algorithms) for removing or reducing noise generated when the external audio signal is received.

The user input unit 130 may receive input data required for controlling the mobile terminal 100 from a user. The user input unit 130 may include a keypad, a dome switch, a touch pad (e.g., constant voltage/capacitance), a jog wheel, and a jog switch.

The sensing unit 140 may sense a current state of the mobile terminal 100, such as an open/closed state of the mobile terminal 100, a position of the mobile terminal 100, whether a user touches the mobile terminal 100, a direction of the mobile terminal 100, and acceleration/deceleration of the mobile terminal 100, and generate a sensing signal required for controlling the mobile terminal 100. For example, if the mobile terminal 100 is a slide phone, the sensing unit 140 may sense whether the slide phone is opened or closed. Further, the sensing unit 140 may sense whether the power supply 190 supplies power and/or whether the interface unit 170 is connected to an external device.

The sensing unit 140 may also include a proximity sensing unit 141. The proximity sensing unit 141 may include at least one proximity sensor.

The proximity sensor of the proximity sensing unit 141 may sense the presence of an object approaching a predetermined sensing face or an object located near the proximity sensor using an electromagnetic force or infrared rays without mechanical contact. The proximity sensor 141 may have a lifetime longer than a contact sensor and may thus be more appropriate for use in the mobile terminal 100.

The proximity sensor of the proximity sensing unit 141 may include a transmission type photoelectric sensor, a direct reflection type photoelectric sensor, a mirror reflection type photoelectric sensor, a high-frequency oscillating proximity sensor, a capacitive proximity sensor, a magnetic proximity sensor, and/or an infrared proximity sensor.

According to an exemplary embodiment of the present invention, the proximity sensor is disposed at one surface of a body of the mobile terminal 100 and detects that a user approaches the user's head to the mobile terminal 100 upon communicating.

Further, according to an exemplary embodiment of the present invention, the proximity sensor is disposed at an internal area of the mobile terminal 100 or at a periphery of the display module 151 and monitors approach of a pointer to a display area. The proximity sensor for monitoring approach of a pointer to the display area will be described in detail at a description of the display module 151 to be described later.

The sensing unit 140 may further include the pulse wave sensing unit 142. The pulse wave sensing unit 142 senses a pulse wave signal, which is a bioelectric signal. The pulse wave sensing unit 142 will be described in detail with reference to FIG. 6 to be described later.

The output unit 150 may generate visual, auditory and/or tactile output and include the display module 151, an audio output module 152, an alarm unit 153 and a haptic module 154.

The display module 151 may display information processed by the mobile terminal 100. For example, the display module 151 may display UI or graphic user interface (GUI) related to a telephone call when the mobile terminal is in the call mode. The display module 151 may display a captured and/or received image, UI or GUI when the mobile terminal 100 is in the video telephony mode or the photographing mode.

The display module 151 may include at least one of a liquid crystal display, a thin film transistor liquid crystal display, an organic light-emitting diode display, a flexible display and/or a three-dimensional display.

The display may be of a transparent type or a light transmission type. This may be referred to as a transparent display. The transparent display may include a transparent liquid crystal display. The rear structure of the display module 151 can also be of the light transmission type. According to this structure, a user can see an object located behind the body of the mobile terminal 100 through an area of the body of the mobile terminal 100, which is occupied by the display module 151.

The mobile terminal 100 may include at least two displays 151 according to constitution of the mobile terminal 100. For example, the mobile terminal 100 may include a plurality of displays that are arranged on a single face at a predetermined distance or may be integrated. Otherwise, the plurality of displays can be arranged on different sides.

In an example where the display module 151 and a sensor sensing touch (hereafter referred to as a touch sensor) form a layered structure, which may be referred to as a touch screen, the display module 151 can be used as an input device in addition to an output device. The touch sensor can be in the form of a touch film, a touch sheet and/or a touch pad, for example.

The touch sensor can be constructed such that the touch sensor converts a variation in pressure applied to a specific portion of the display module 151 or a variation in capacitance generated at a specific portion of the display module 151 into an electric input signal. The touch sensor can be constructed such that the touch sensor can sense pressure of touch as well as position and area of touch.

When a touch input is applied to the touch sensor, a signal corresponding to the touch input is transmitted to a touch controller. The touch controller may process the signal and transmit data corresponding to the processed signal to the controller 180. Accordingly, the controller 180 can detect a touched portion of the display module 151.

The proximity sensor of the proximity sensing unit 141 may be located in an internal region of the mobile terminal 100, surrounded by the touch screen, or near the touch screen. The proximity sensor may sense the presence of an object approaching a predetermined sensing face or an object located near the proximity sensor using an electromagnetic force or infrared rays without mechanical contact. The proximity sensor 141 may have a lifetime longer than a contact sensor and may thus be more appropriate for use in the mobile terminal 100.

A capacitive touch screen may be constructed such that proximity of a pointer is detected through a variation in an electric field according to the proximity of the pointer. The touch screen (touch sensor) may be considered as a proximity sensor 141.

For the convenience of description, an action in which a pointer approaches the touch screen without actually touching the touch screen may be referred to as a proximity touch, and an action in which the pointer is brought into contact with the touch screen may be referred to as a contact touch. The proximity touch point of the pointer on the touch screen may correspond to a point of the touch screen at which the pointer is perpendicular to the touch screen.

The proximity sensor 141 may sense the proximity touch and a proximity touch pattern (e.g., a proximity touch distance, a proximity touch direction, a proximity touch velocity, a proximity touch time, a proximity touch position, a proximity touch moving state). Information corresponding to the sensed proximity touch action and proximity touch pattern may then be displayed on the touch screen.

The audio output module 152 may output audio data received from the radio communication unit 110 or stored in the memory 160 in a call signal receiving mode, a call mode or a recording mode, a speech recognition mode and a broadcast receiving mode. The audio output module 152 may output audio signals related to functions performed in the mobile terminal 100, such as a call signal incoming tone and a message incoming tone. The audio output module 152 may include a receiver, a speaker, and/or a buzzer. The audio output module 152 may output sounds through an earphone jack. The user may listen to the sounds by connecting an earphone to the earphone jack.

The alarm unit 153 may output a signal indicating generation (or occurrence) of an event of the mobile terminal 100. For example, alarms may be generated when a call signal or a message is received and when a key signal or a touch is input. The alarm unit 153 may also output signals different from video signals or audio signals, for example, a signal indicating generation of an event through vibration. The video signals or the audio signals may also be output through the display module 151 or the audio output module 152.

The haptic module 154 may generate various haptic effects that the user may feel. One of the haptic effects is vibration. The intensity and/or pattern of a vibration generated by the haptic module 154 may also be controlled. For example, different vibrations may be combined with each other and output or may be sequentially output.

The haptic module 154 may generate a variety of haptic effects including an effect attributed to an arrangement of pins vertically moving against a contact skin surface, an effect attributed to a jet force or a suctioning force of air through a jet hole or a suction hole, an effect attributed to a rubbing of the skin, an effect attributed to contact with an electrode, an effect of stimulus attributed to an electrostatic force, and an effect attributed to a reproduction of cold and warmth using an element for absorbing or radiating heat in addition to vibrations.

The haptic module 154 may not only transmit haptic effects through direct contact but may also allow the user to feel haptic effects through the user's fingers or arms. The mobile terminal 100 may also include a plurality of haptic modules 154.

The memory 160 may store a program for operating the controller 180 and temporarily store input/output data such as a phone book, messages, still images, and/or moving pictures. The memory 160 may also store data regarding various patterns of vibrations and sounds that are output from when a touch input is applied to the touch screen.

The memory 160 may include at least a flash memory, a hard disk type memory, a multimedia card micro type memory, a card type memory such as SD or XD memory, a random access memory (RAM), a static RAM (SRAM), a read-only memory (ROM), an electrically erasable programmable ROM (EEPROM), a programmable ROM (PROM) magnetic memory, a magnetic disk, or an optical disk. The mobile terminal 100 may also operate in association with a web storage performing the storage function of the memory 160 on the Internet.

The interface unit 170 may serve as a path to external devices connected to the mobile terminal 100. The interface unit 170 may receive data or power from the external devices, transmit the data or power to internal components of the mobile terminal 100, or transmit data of the mobile terminal 100 to the external devices. For example, the interface unit 170 may include a wired/wireless headset port, an external charger port, a wired/wireless data port, a memory card port, a port for connecting a device having a user identification module, an audio I/O port, a video I/O port, and/or an earphone port.

The interface unit 170 may also interface with a user identification module that is a chip that stores information for authenticating authority to use the mobile terminal 100. For example, the user identification module may be a user identity module (UIM), a subscriber identity module (SIM) and a universal subscriber identify module (USIM). An identification device including the user identification module may also be manufactured in the form of a smart card. Accordingly, the identification device may be connected to the mobile terminal 100 through a port of the interface unit 170.

The interface unit 170 may also be a path through which power from an external cradle is provided to the mobile terminal 100 when the mobile terminal 100 is connected to the external cradle or a path through which various command signals input by the user through the cradle are provided to the mobile terminal 100. The various command signals or power input from the cradle may be used as signals for checking whether the mobile terminal 100 is correctly settled (or loaded) in the cradle.

The controller 180 may control overall operations of the mobile terminal 100. For example, the controller 180 may control and process voice communication, data communication and/or a video call. The controller 180 may also include a multimedia module 181 for playing a multimedia file. The multimedia module 181 may be included in the controller 180 as shown in FIG. 1 or may be separated from the controller 180.

The controller 180 may perform a pattern recognition process of recognizing handwriting input or picture-drawing input applied to the touch screen as characters or images. The power supply 190 may receive external power and internal power and provide power required for operating the components of the mobile terminal 100 under the control of the controller 180.

According to a hardware implementation, embodiments of the present invention may be implemented using at least application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and/or electrical units for executing functions. The embodiments may be implemented using the controller 180.

According to a software implementation, embodiments including procedures or functions may be implemented using a separate software module executing at least one function or operation. Software code may be implemented according to a software application written in an appropriate software language. The software codes may be stored in the memory 160 and executed by the controller 180.

Figure 2:
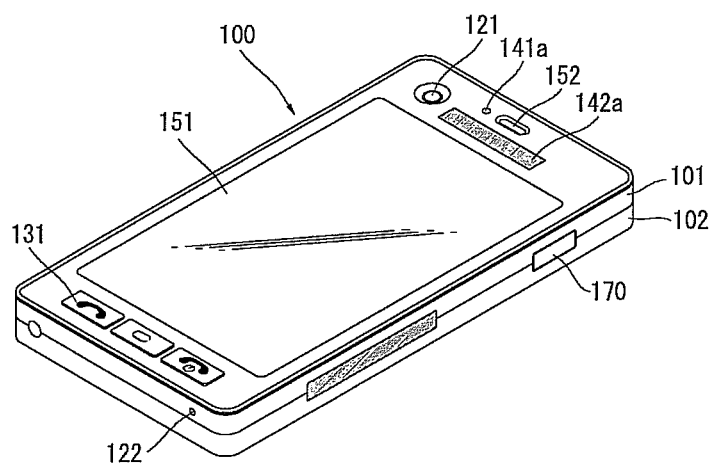
FIG. 2 is a front perspective view illustrating a mobile terminal according to exemplary embodiments of the present invention.

FIG. 2 is a front perspective view of a mobile terminal or a handheld terminal 100 according to an embodiment of the present invention. The handheld terminal 100 has a bar type terminal body. However, embodiments of the present invention are not limited to a bar type terminal and may include various types of terminals such as slide type, folder type, swing type and swivel type terminals having at least two bodies coupled such that they can move relative to each other.

The terminal body includes a case (a casing, a housing, or a cover) forming the exterior of the terminal 100. In the embodiment of FIG. 2, the case may be divided into a front case 101 and a rear case 102. Various electronic components are arranged in the space (volume) defined between the front case 101 and the rear case 102. At least one middle case may be additionally arranged between the front case 101 and the rear case 102. The cases may be made of plastics through injection molding or made of a metal material such as stainless steel (STS) or titanium (Ti).

The display module 151, the audio output module 152, the camera 121, user input unit 130 (e.g., operating units 131, 132), the microphone 122 and the interface unit 170 may be arranged in the terminal body, specifically, in the front case 101.

The display module 151 occupies a majority of the area of the main face of the front case 101. The audio output module 152 and the camera 121 are arranged in a region in proximity to an end of the display module 151, and the operating unit 131 and the microphone 122 are located in a region in proximity to the other end of the display module 151. The operating unit 132 and the interface unit 170 are arranged on the lateral sides of the front case 101 and the rear case 102.

The user input unit 130 is operated to receive commands controlling the handheld terminal 100 and may include a plurality of operating units 131 and 132. The first and second operating units 131 and 132 may be referred to as manipulating portions and may employ a tactile mechanism by which a user operates the operating units 131 and 132 by touch.

The first and second operating units 131 and 132 may receive various inputs. For example, the first operating unit 131 receives commands such as 'START,' 'END,' and 'SCROLL,' and the second operating unit 132 receives commands such as 'CONTROL' (the volume of sound output from the audio output module 152) or 'CONVERT' (a mode of the display module 151 into a touch recognition mode).

Further, according to an exemplary embodiment of the present invention, a proximity sensor 141a and a plurality of electrodes 142a and 142b may be disposed at the bodies 101 and 102 of the mobile terminal 100.

The proximity sensor 141a is disposed at a front surface of the mobile terminal 100 and detects an object approaching a specific position of a body of the mobile terminal 100. For example, the proximity sensor 141a is disposed adjacent to the audio output module 152 for operating as a speaker for outputting communication sound in a call mode and the electrode 142a used for sensing a pulse wave and detects whether the user's head approaches the audio output module 152 in a call mode.

Further, the plurality of electrodes 142a and 142b each are disposed adjacent to the audio output module 152 at a front surface of the mobile terminal 100 or are disposed at side surfaces of a front case 101 and a rear case 102. The plurality of electrodes 142a and 142b contact with the user's skin surface and are used for sensing the user's pulse wave.

FIG. 2 illustrates an example in which the plurality of electrodes 142a and 142b are disposed, and when the user communicates using the mobile terminal 100 or manipulates the mobile terminal 100, the plurality of electrodes 142a and 142b may be disposed at another position of easily contacting with the user's skin surface.

Figure 3:
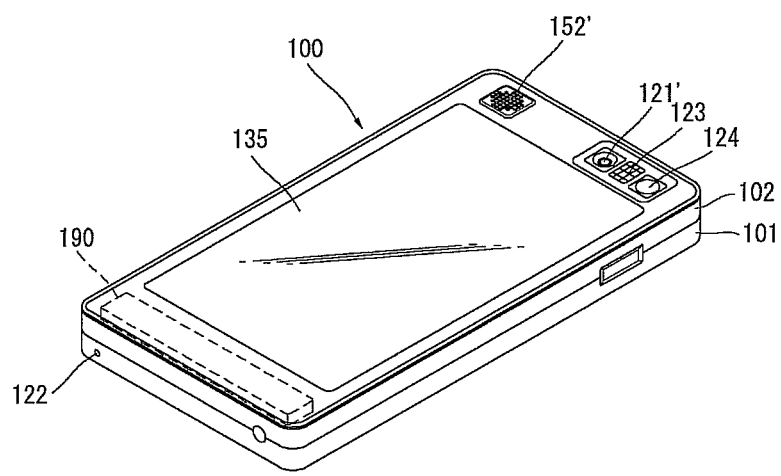
FIG. 3 is a rear perspective view illustrating a mobile terminal according to exemplary embodiments of the present invention.

FIG. 3 is a rear perspective view of the handheld terminal shown in FIG. 2 according to an embodiment of the present invention.

Referring to FIG. 3, a camera 121' may be additionally mounted at the rear side of the terminal body, that is, the rear case 102. The camera 121' captures images along a direction opposite to that of the camera 121 shown in FIG. 2 and may have a pixel resolution different from that of the camera 121.

For example, according to one embodiment, the camera 121 has a relatively low resolution suitable for capturing an image of the face of a user and transmitting the captured image in a video call, while the camera 121' has a relatively high resolution suitable for capturing a photograph of a general subject. The cameras 121 and 121' may be mounted to the terminal body such that they may be rotated or popped-up.

A flash 123 and a mirror 124 may be additionally arranged in proximity to the camera 121'. The flash 123 lights a subject when the camera 121' takes a picture of the subject. The mirror 124 may be used by the user to view his/her face when the user wants to self-photograph himself/herself using the camera 121'.

An audio output module 152' may be additionally provided on the rear side of the terminal body. The audio output module 152' may facilitate a stereo function in conjunction with the audio output module 152 shown in FIG. 2 and may be used in a speaker phone mode when the terminal is used for a voice call.

A broadcasting signal receiving antenna 116 may be additionally attached to the side of the terminal body in addition to an antenna for voice calls. The antenna, which may constitute a part of the broadcast receiving module 111 shown in FIG. 1, may be mounted in the terminal body such that the antenna may be pulled out from (and retracted into) the terminal body.

The power supply 190 for providing power to the handheld terminal 100 is set in the terminal body. The power supply 190 may be provided in the terminal body or detachably installed on the terminal body.

A touch pad 135 for sensing a touch may be additionally attached to the rear case 102. The touch pad 135 may be of a light transmission type similar to the display module 151. In this configuration, if the display module 151 outputs visual information through both of its sides (or faces), the visual information may be viewable via the touch pad 135. The information output through both sides of the display unit 151 may be controlled by the touch pad 135. Alternatively (or in addition), a display is additionally attached to the touch pad 135 such that a touch screen may be arranged in the rear case 102.

The touch pad 135 operates in connection with the display module 151 of the front case 101. The touch pad 135 may extend parallel to the display module 151 behind the display module 151. The touch panel 135 may have a size equal to or smaller than the size of the display module 151.

Figure 4:
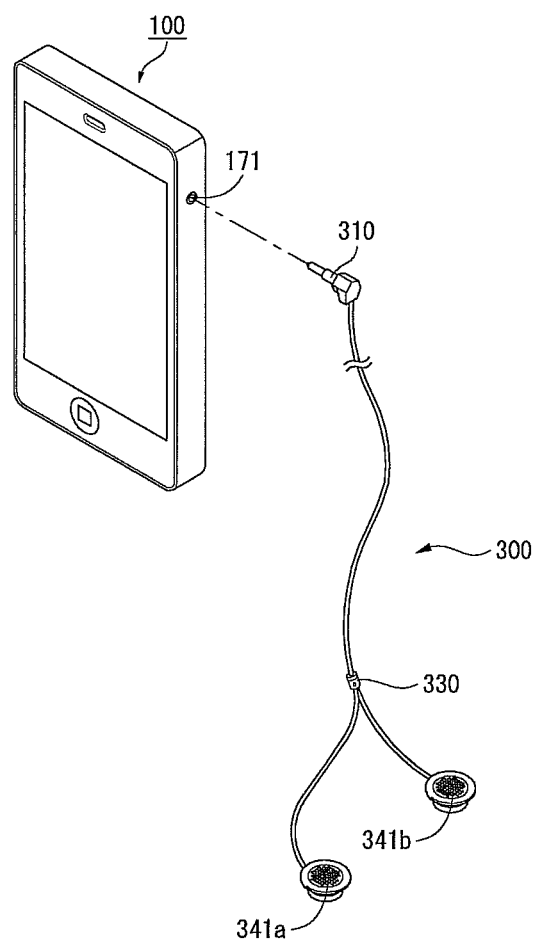
FIG. 4 is a perspective view illustrating a configuration of a mobile terminal to which an earphone is connected according to an exemplary embodiment of the present invention.

FIG. 4 is a perspective view illustrating a configuration of a mobile terminal to which an earphone is connected according to an exemplary embodiment of the present invention.

Referring to FIG. 4, an earphone 300 is detachably mounted in a main body of the mobile terminal 100 through an earphone port 171.

The main body of the mobile terminal 100 may be classified into various types, for example, a slide type and a folder type. The main body of the mobile terminal 100 has the earphone port 171 in which the earphone 300 is detachably mounted, and the earphone port 171 may include a connection terminal of the predetermined quantity.

For example, when the earphone 300 is a quadrupole earphone, the earphone 300 includes a microphone 330 for collecting a user's voice signal in order to support a push to talk (PTT) service and thus one of connection terminals of the earphone port 171 includes a microphone terminal for transferring a user's voice signal collected through the microphone 330 to the mobile terminal 100.

The earphone 300 may further include a plurality of electrodes 341a and 341b for acquiring a pulse wave of the user of the earphone 300 according to an exemplary embodiment of the present invention. When the user inserts the earphone 300 into the ear, in order to sense a pulse wave by directly contacting with a skin surface of the user, the electrodes 341a and 341b are disposed at a main body of the earphone 300.

When the earphone 300 includes the plurality of electrodes 341a and 341b for sensing a pulse wave, the earphone port 171 may further include a terminal for transferring a pulse wave signal collected through the plurality of electrodes 341a and 341b for sensing a pulse wave to the mobile terminal 100.

Figure 5:
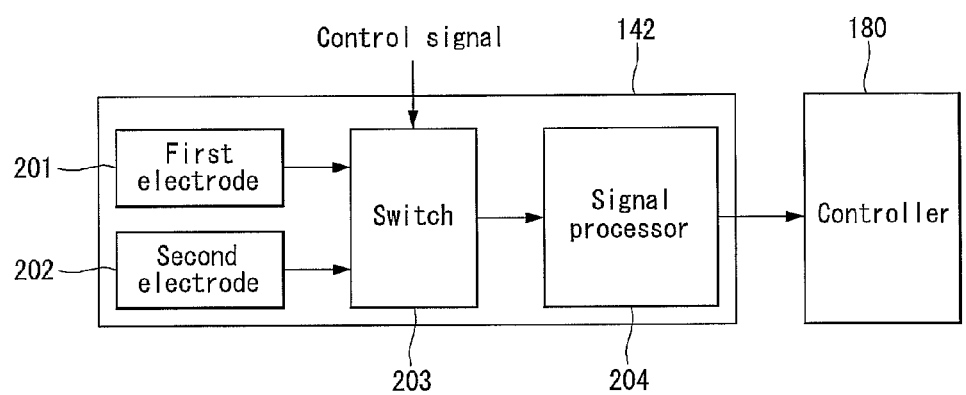
FIG. 5 is a block diagram illustrating a configuration of a pulse wave sensing unit according to an exemplary embodiment of the present invention.

FIG. 5 is a diagram illustrating a configuration of a pulse wave sensing unit 142 according to an exemplary embodiment of the present invention.

Referring to FIG. 5, the pulse wave sensing unit 142 includes a plurality of electrodes 201 and 202, a switch 203, and a signal processor 204. Because elements shown in FIG. 5 are not essential, the pulse wave sensing unit 142 may have elements more than or fewer than the above elements.

The plurality of electrodes 201 and 202 detect the user's pulse wave by contacting with the user's skin surface and output an electric signal corresponding thereto.

A pulse wave is a wave in which blood is propagated in a wave form from the heart. Further, a pulse wave signal is to express a pulse wave in a waveform form. That is, a pulse wave signal is to express a pressure change of a peripheral vein and artery system by heart pulsation in a waveform.

As a method of sensing a pulse wave signal, a method of acquiring a pulse wave signal by recognizing bloodstream increasing upon heart pulsation using a photo plethysmograph with a photo diode and a method of acquiring a pulse wave signal with a voltage waveform measured using a plurality of electrodes can be used. In this document, a method of acquiring a pulse wave signal using a method of using an electrode of the latter is disclosed.

In this document, an example of acquiring a pulse wave signal using two electrodes is described, but a technical idea disclosed in this document can be applied to a case of having two or more electrodes.

As described above, in order to sense a user's pulse wave using the electrodes 201 and 202, it is necessary to directly contact the electrodes 201 and 202 with the user's skin surface.

According to an exemplary embodiment of the present invention, a plurality of electrodes 201 and 202 may be disposed at an outer surface of a body of the mobile terminal 100, as in the electrodes 142a and 142b shown in FIG. 2. In this case, when the user performs communication with the mobile terminal 100 while contacting the mobile terminal 100 with the user's head, the electrodes 142a and 142b are disposed at a position of directly contacting with the user's skin surface.

Further, according to an exemplary embodiment of the present invention, the plurality of electrodes 201 and 202 may be disposed at a main body of the earphone 300, as in the electrodes 341a and 341b shown in FIG. 4.

Further, according to an exemplary embodiment of the present invention, the controller 180 may convert a plurality of electrodes 201 and 202 used for sensing a pulse wave to the electrodes 142a and 142b disposed at an outer surface of the body of the mobile terminal 100 or the electrodes 341a and 341b disposed at a main body of the earphone 300 based on whether the earphone 300 is attached to the mobile terminal 100.

For example, when the earphone 300 is attached to the mobile terminal 100, the controller 180 may sense a pulse wave using the electrodes 341a and 341b positioned at the main body of the earphone 300.

Further, for example, when the earphone 300 is not attached to the mobile terminal 100, the controller 180 may sense a pulse wave using the electrodes 142a and 142b positioned at an outer surface of the body of the mobile terminal 100.

Referring again to FIG. 5, the switch 203 controls to input a pulse wave signal acquired through the plurality of electrodes 201 and 202 to the signal processor 204 based on a control signal input from the outside of the pulse wave sensing unit 142.

A control signal that is input to the switch 203 may be input from the proximity sensing unit 141. As shown in FIG. 2, the proximity sensor 141a disposed adjacent to the audio output module 152 detects approach of an object to the audio output module 152, and the proximity sensing unit 141 outputs a control signal based on a sensing result of the proximity sensor 141a disposed adjacent to the audio output module 152.

For example, whenever an object approaching the audio output module 152 through the proximity sensor 141a is detected, the proximity sensing unit 141 may output a control signal for transferring a pulse wave signal acquired through the electrodes 201 and 202 to the signal processor 204 to the switch 203.

In this case, a sensing signal output from the proximity sensor 141a may be directly input as a control signal of the switch 203. Therefore, whenever an object approaching the audio output module 152 is detected, a pulse wave signal acquired through the electrodes 201 and 202 is output to the controller 180 via the signal processor 204, and the controller 180 performs operation using a pulse wave signal acquired through the electrodes 201 and 202 in only a call mode.

Further, for example, only when the mobile terminal 100 operates in a call mode, the proximity sensing unit 141 may switch to output a sensing signal output from the proximity sensor 141a disposed adjacent to the audio output module 152 as a control signal of the switch 203. In this case, whenever an object approaching the audio output module 152 is detected, the proximity sensor 141a outputs a detection signal, and only when the mobile terminal 100 is communicating, the output detection signal may be output as a control signal to transfer a pulse wave signal acquired through the electrodes 201 and 202 to the signal processor 204.

Further, for example, only when the mobile terminal 100 operates in a call mode, the proximity sensing unit 141 may activate the proximity sensor 141a. Accordingly, the proximity sensor 141a is activated only in a call mode and detects an object approaching the audio output module 152 and outputs a detection signal as a control signal.

A control signal that is input to the switch 203 may be also input from the controller 180.

For example, when the mobile terminal 100 operates in a call mode and approach of an object to the audio output module 152 is detected through the proximity sensor 141a disposed adjacent to the audio output module 152, the controller 180 may output a control signal to transfer a pulse wave signal acquired through the electrodes 201 and 202 to the signal processor 204.

Further, for example, when the mobile terminal 100 operates in a call mode and the earphone 300 is attached to the mobile terminal 100, the controller 180 may output a control signal to transfer a pulse wave signal acquired through the electrodes 201 and 202 to the signal processor 204.

Figure 6:
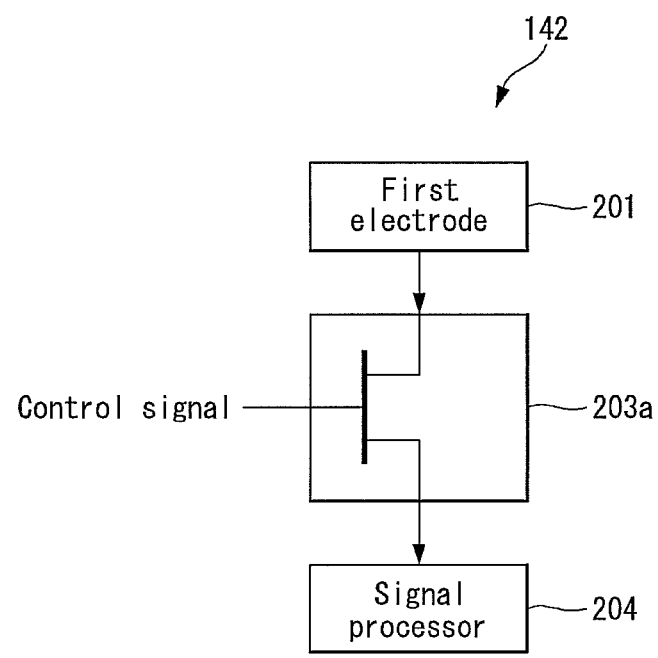
FIG. 6 is a block diagram illustrating an example of a switch according to an exemplary embodiment of the present invention.

Referring again to FIG. 5, the switch 203 according to an exemplary embodiment of the present invention can be embodied in various forms. FIG. 6 illustrates an example of the switch 203.

Referring to FIG. 6, the switch 203 may include a field effect transistor (FET) 203a. A control signal that is input from the proximity sensor 141a or the controller 180 is input to a gate terminal of the FET 203a and controls switching of the FET 203a. Further, a drain terminal is connected to the first electrode 201 and receives a detection signal output from the first electrode 201. Further, a source terminal is connected to the signal processor 204 and outputs an output signal of the FET 203a to the signal processor 204.

Accordingly, if the FET 203a is turned on by a control signal, a pulse wave signal output from the first electrode 201 is transferred to the signal processor 204. If the FET 203a is turned off by a control signal, a pulse wave signal output from the first electrode 201 is not transferred to the signal processor 204.

According to an exemplary embodiment of the present invention, as described above, only when the user is communicating with the mobile terminal, the proximity sensing unit 141 or the controller 180 outputs a control signal to turn on the FET 203a.

Referring again to FIG. 5, when a pulse wave signal output from the electrodes 201 and 202 is input through the switch 203, the signal processor 204 performs a signal processing for amplifying and filtering the input pulse wave signal and outputs pulse wave data in which a signal processing is performed to the controller 180.

A pulse wave signal output through the electrodes 201 and 202 has a micro analog voltage waveform form. A pulse wave signal output from the electrodes 201 and 202 has a micro size and thus it is difficult to analyze the pulse wave signal. Therefore, the signal processor 204 amplifies the pulse wave signal, performs filtering for removing noise such as distortion of a baseline, then converts an analog pulse wave signal to digital pulse wave data, and outputs the digital pulse wave data to the controller 180.

The controller 180, having received pulse wave data from the pulse wave sensing unit 142 analyzes the pulse wave data, thereby checking a user's emotional state and health state.

FIG. 5 illustrates a case where the switch 203 is positioned between the electrodes 201 and 202 and the signal processor 204, but a technical idea disclosed in this document can be applied even to a case where the switch 203 is positioned between the signal processor 204 and the controller 180. In this case, as described above, the switch 203 controls to input pulse wave data output from the signal processor 204 to the controller 180 based on a control signal input from the outside of the pulse wave sensing unit 142.

An exemplary embodiment disclosed in this document can be embodied in the mobile terminal 100 described with reference to FIGS. 1 and 5.

Hereinafter, a method of measuring a bioelectric signal of a mobile terminal and operations of a mobile terminal for embodying the same according to an exemplary embodiment of the present invention will be described in detail with reference to necessary drawings.

Figure 7:
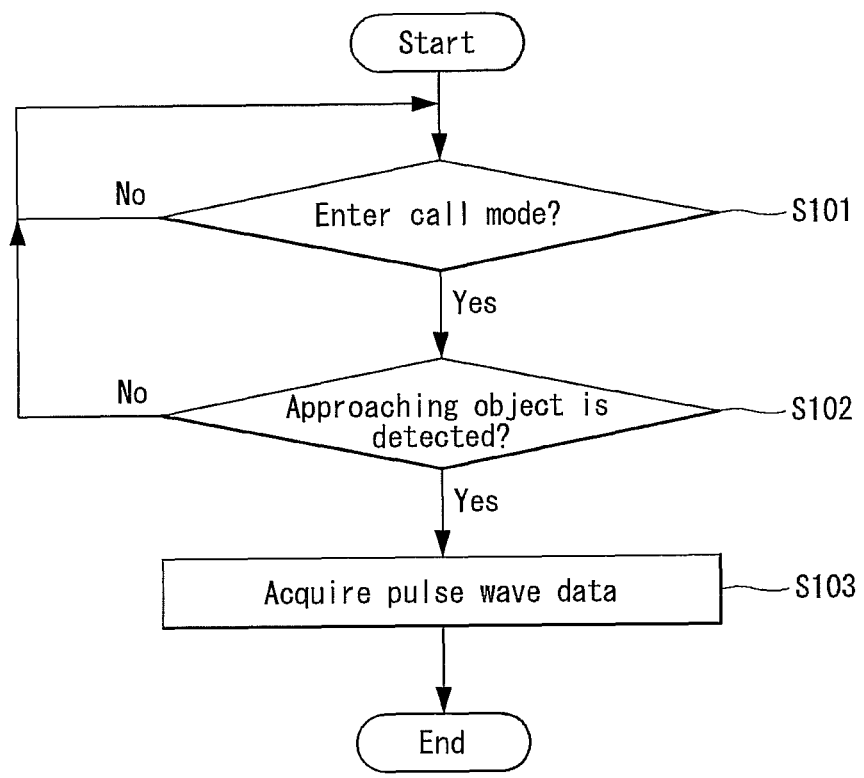
FIG. 7 is a flowchart illustrating a method of measuring a bioelectric signal in a mobile terminal according to an exemplary embodiment of the present invention.

FIG. 7 is a flowchart illustrating a method of measuring a bioelectric signal in the mobile terminal 100 according to an exemplary embodiment of the present invention.

Referring to FIG. 7, the controller 180 determines whether the mobile terminal 100 enters a call mode (S101).

If the mobile terminal 100 enters a call mode, the controller 180 determines whether an object approaching a specific area of a body of the mobile terminal 100 is detected (S102), and if an object approaching a specific area of a body of the mobile terminal 100 is detected, the controller 180 acquires pulse wave data through the pulse wave sensing unit 142 (S103).

At step S102, an object approaching a specific area of a body of the mobile terminal 100 may be detected through the proximity sensing unit 141. Further, a specific area for detecting an approaching object may be an area at which the audio output module 152 for operating as a speaker for outputting communication sound in a call mode is positioned. That is, at step S102, the proximity sensor 141a disposed adjacent to the audio output module 152 can detect an object approaching the audio output module 152.

Further, at step S102, when the proximity sensing unit 141 detects an object approaching a specific area of a body of the mobile terminal 100 through a proximity sensor, in order to transfer a pulse wave signal acquired through a plurality of electrodes 201 and 202 to the controller 180 through the signal processor 204, the proximity sensing unit 141 outputs a control signal of controlling the pulse wave sensing unit 142 to the pulse wave sensing unit 142.

When the pulse wave sensing unit 142 receives a sensing signal representing that an object approaching a specific area of a body of the mobile terminal 100 is detected as a control signal from the proximity sensing unit 141, the pulse wave sensing unit 142 switches to transfer a pulse wave signal detected through the plurality of electrodes 201 and 202 to the controller 180 through the signal processor 204.

FIG. 7 illustrates a case where the controller 180 acquires pulse wave data only when the mobile terminal 100 enters a call mode and an object approaching a specific area of a body of the mobile terminal 100 is detected, but the present invention is not limited thereto.

According to the present invention, when the user communicates using the earphone 300, i.e., when the earphone 300 is attached to the mobile terminal 100, even if an object approaching a specific area of a body of the mobile terminal 100 is not detected, the controller 180 can acquire the pulse wave data through the pulse wave sensing unit 142. In this case, when the mobile terminal 100 enters a call mode, in order to transfer a pulse wave signal acquired through the plurality of electrodes 201 and 202 to the controller 180 through the signal processor 204, the controller 180 outputs a control signal of controlling the pulse wave sensing unit 142 to the pulse wave sensing unit 142.

Figure 8:
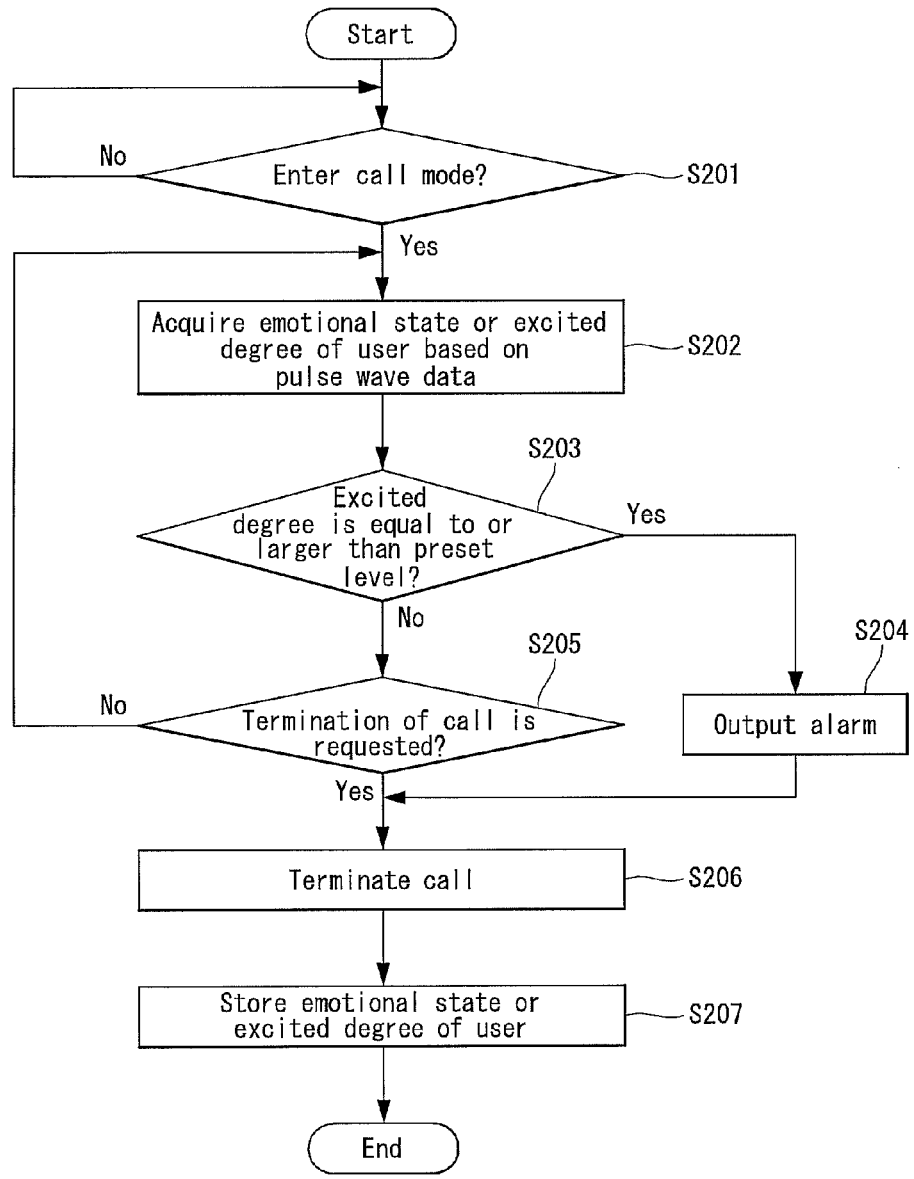
FIG. 8 is a flowchart illustrating an example of a method of determining whether to terminate communication using pulse wave data in a mobile terminal according to an exemplary embodiment of the present invention.

FIG. 8 is a flowchart illustrating an example of a method of determining whether to terminate communication using pulse wave data in the mobile terminal 100 according to an exemplary embodiment of the present invention.

Referring to FIG. 8, the controller 180 determines whether the mobile terminal 100 enters a call mode (S201), and if the mobile terminal 100 enters a call mode, the controller 180 acquires an emotional state or an excited degree of the user by analyzing pulse wave data acquired through the pulse wave sensing unit 142 (S202).

At step S202, the controller 180 acquires characteristic parameters to be a reference for determining an emotional state and an excited degree of the user from pulse wave data through analysis of pulse wave data. Such parameter may include a peak value of a pulse wave signal, a heart rate acquired using a peak value of the pulse wave signal, and a heartbeat cycle.

The controller 180 determines whether the user's excited degree acquired at step S202 is equal to or larger than a preset level (S203), and if the user's excited degree acquired at step S202 is equal to or larger than a preset level, the controller 180 outputs alarm for warning an excited state of the user (S204). Further, the controller 180 may terminate a call with another party for the user's stability (S206).

Alarm for warning the user's excited state may be output in various forms.

For example, if the user's excited state is equal to or larger than a preset level, the controller 180 may transmit guide sound for warning call another party of this.

Further, for example, if the user's excited state is equal to or larger than a preset level, the controller 180 may output guide sound or vibration sound for warning the user of this or display a warning message through the display module 151.

FIG. 8 illustrates a case of forcedly terminating a call, if the user's excited degree is equal to or larger than a preset level, but the present invention is not limited thereto.

According to an exemplary embodiment of the present invention, if the user's excited degree is equal to or larger than a preset level, the controller 180 may output only alarm for warning the user's state and may not terminate a call.

Further, according to an exemplary embodiment of the present invention, if the user's excited degree is equal to or larger than a preset level, the controller 180 may store call contents with another party in the memory 160.

Referring to again FIG. 8, the controller 180 determines whether termination of a call is requested by the user (S205), and if termination of a call is requested by the user or if a call mode is terminated because the user's excited degree is equal to or larger than a preset level, the controller 180 stores an emotional state or an excited degree of the user in the memory 160 (S207).

For example, the controller 180 may include and store an emotional state or an excited degree of the user acquired in a call mode in a call record.

Further, for example, the controller 180 may store an emotional state or an excited degree of the user acquired in a call mode to correspond to contact information of another party.

Figure 9:
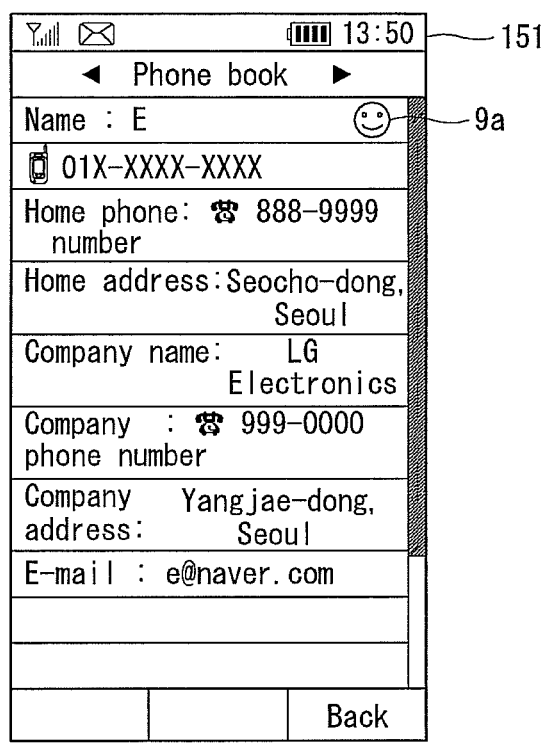
FIG. 9 illustrates an example of storing a user's emotional state at a phonebook to correspond to contact information of call another party in a mobile terminal according to an exemplary embodiment of the present invention.

FIG. 9 illustrates an example of storing a user's emotional state at a phonebook to correspond to contact information of call another party.

Referring to FIG. 9, when a call is terminated with another party A, the controller 180 stores an emotional state (e.g., pleasant) in which the user felt to another party A while communicating at the phonebook to correspond with contact information of another party A.

Thereafter, when reading contact information of another party A included in the phonebook and displaying the contact information on the screen, the controller 180 controls to read together the user's emotional state 9a stored together with the contact information and display the user's emotional state 9a and the contact information on the screen. The user's emotional state may be displayed in various forms such as an emoticon and a text. FIG. 9 illustrates an example of displaying a user's emotional state in an emoticon form.

When information representing an emotional state or an excited degree of the user to call another party has already been stored, the controller 180 updates the emotional state or excited degree of the user using a presently acquired emotional state or excited degree.

Further, the controller 180 may continue to store an emotional state or an excited degree acquired in a call mode.

Figure 10:
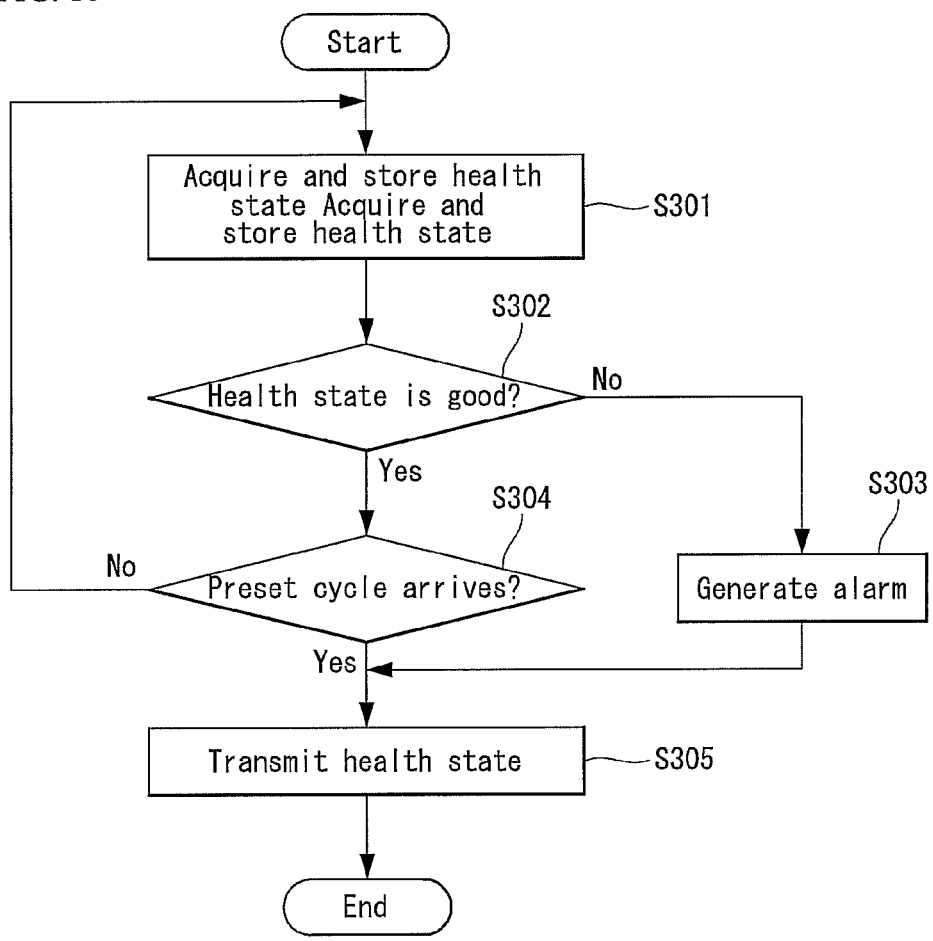
FIG. 10 is a flowchart illustrating an example of a method of managing a user's health state using pulse wave data in a mobile terminal according to an exemplary embodiment of the present invention.

FIG. 10 is a flowchart illustrating an example of a method of managing a user's health state using pulse wave data in the mobile terminal 100 according to an exemplary embodiment of the present invention.

Referring to FIG. 10, the controller 180 acquires the user's health state based on the user's pulse wave data acquired through the pulse wave sensing unit 142 (S301).

The controller 180 acquires characteristic parameters such as a peak value, a heart rate, and a heartbeat cycle to be a reference for determining the user's health state from pulse wave data through analysis of pulse wave data. The controller 180 acquires the user's health state based on such characteristic parameters.

Further, the controller 180 stores the acquired pulse wave data and health state in the memory 160. The pulse wave data and health state of the user may be stored together with a time and position that acquire the same.

The controller 180 determines whether the user's health state is good based on the acquired health state (S302), and if the user's health state is not good, the controller 180 generates alarm (S303).

For example, the controller 180 controls to output guide sound or vibration sound for warning the user of abnormality of a health state, or to display a message for warning the user of abnormality of a health state through the display module 151.

Further, for example, the controller 180 transmits health state information or a message for warning abnormality of a health state of the user using a preset phone number.

Referring again to FIG. 10, if the user's health state is good, the controller 180 determines whether a preset cycle arrives (S304), and if a preset cycle arrives, the controller 180 transmits the user's health state including the acquired pulse wave data, heart rate, and heartbeat cycle to preset another party using a phone number and an e-mail address of preset another party (S305).

At step S302, the controller 180 compares a presently acquired pulse wave data, heart rate, and heartbeat cycle with the previously acquired pulse wave data, heart rate, and heartbeat cycle, and when a change amount thereof is large, the controller 180 may determine that abnormality occurs in the user's health.

Further, at step S302, the controller 180 compares the acquired pulse wave data, heart rate, and heartbeat cycle with a preset reference, and when the acquired pulse wave data, heart rate, and heartbeat cycle are deviated from a preset reference, the controller 180 may determine that abnormality occurs in the user's health.

According to an exemplary embodiment of the present invention, the user's pulse wave data acquired through the pulse wave sensing unit 142 can be used in various fields in addition to the above-described call mode control and health state management.

For example, the controller 180 may acquire the user's emotional state from pulse wave data acquired through the pulse wave sensing unit 142 and couple and store the emotional state to a present position of the mobile terminal 100. A stored health state coupled to position information may be used as a reference for searching for and providing specific position information such as peripheral good taste restaurants to the user. For example, peripheral good taste restaurants in which the user's emotional state is negatively recorded may be removed from a peripheral good taste restaurant list to be recommended to the user. Further, for example, peripheral good taste restaurants in which the user's emotional state is positively recorded may be preferentially recommended to the user.

Further, for example, the controller 180 may acquire a user's emotional state from pulse wave data acquired through the pulse wave sensing unit 142 and selectively provide only specific position information corresponding to the user's emotional state to the user.

Further, for example, the controller 180 may acquire a user's emotional state or stress index from pulse wave data acquired through the pulse wave sensing unit 142 and recommend specific contents to the user based on the user's emotional state or stress index. When the user has a negative emotional state or a high stress index, the controller 180 may recommend or provide contents of a specific kind to be a help for the user's stability or relaxation to the user. Here, contents supplied for the user's stability or relaxation may be set by the user.

According to an exemplary embodiment of the present invention, a case where the mobile terminal 100 measures the user's pulse wave signal while operating in a call mode is exemplified, but the present invention is not limited thereto. According to the present invention, even when a request for measuring a pulse wave signal is input by the user through the user input unit 130, a user's pulse wave signal can be measured.

According to the foregoing exemplary embodiment of the present invention, the mobile terminal can measure a user's pulse wave signal without a separate electronic device or a separate equipment. Further, in a mobile terminal for performing various functions in addition to a pulse wave signal measuring function, by activating pulse wave signal measurement only in a designated mode, power consumption by pulse wave signal measurement can be minimized. Further, in a state where the mobile terminal does not operate in a call mode, by electrically separating electrodes from a signal processor, noises injected from the outside through an electrode can be minimized and an internal circuit can be protected.

The disclosed methods of measuring bioelectric signal of the mobile terminal may be written as computer programs and may be implemented in digital microprocessors that execute the programs using a computer readable recording medium. The methods of measuring bioelectric signal of the mobile terminal may be executed through software. The software may include code segments that perform required tasks. Programs or code segments may also be stored in a processor readable medium or may be transmitted according to a computer data signal combined with a carrier through a transmission medium or communication network.

The computer readable recording medium may be any data storage device that may store data and may be read by a computer system. Examples of the computer readable recording medium may include read-only memory (ROM), random-access memory (RAM), CD-ROMs, DVD±ROM, DVD-RAM, magnetic tapes, floppy disks, and optical data storage devices. The computer readable recording medium may also be distributed over network coupled computer systems such that the computer readable code is stored and executed in a distributed manner.

The foregoing embodiments and features are merely exemplary in nature and are not to be construed as limiting the present invention. The disclosed embodiments and features may be readily applied to other types of apparatuses. The description of the foregoing embodiments is intended to be illustrative, and not to limit the scope of the claims. Many alternatives, modifications, and variations will be apparent to those skilled in the art.

What is claimed is:

1. A mobile terminal comprising:
    a proximity sensor disposed at a surface of the mobile terminal and configured to detect an object approaching the surface of the mobile terminal;
    a plurality of electrodes disposed at the surface of the mobile terminal;
    a pulse wave sensing unit configured to obtain a pulse wave signal through the plurality of electrodes; and
    a controller configured to:
        provide a control signal, for activating the pulse wave sensing unit, to the pulse wave sensing unit when the mobile terminal is in a call mode and the object is detected through the proximity sensor;
        control the pulse wave sensing unit to obtain the pulse wave signal when the pulse wave sensing unit receives the control signal;
        acquire at least one of a pulse wave data, a heart rate, and a heartbeat cycle based on the pulse wave signal;
        determine whether a user's health state is abnormal considering that the acquired at least one of the pulse wave data, the heart rate, and the heartbeat cycle is deviated from a first preset reference,
        output a notification for warning abnormality of the user's health state through the mobile terminal and transmit the notification to a call party, when the user's health state is abnormal;
        transmit the user's health state to a preset another party using a phone number and an e-mail address of the preset another party when a preset cycler arrives;
        store position information of the mobile terminal and the user's health state coupled to the position information;
        recommend or provide contents of a specific kind of a help for the user's stability or relaxation, when the user's health state is abnormal and the call mode is terminated;
        recommend specific restaurant position information related to a stored good health state of the user when the call mode is terminated and an application for searching restaurant position information is executed;
        determine a user's excitement based on the acquired pulse wave data;
        output an alarm for warning that the user is in an excited state, when the determined excitement is equal to or greater than a preset level;
        and terminate the call mode when the determined excitement is equal to or greater than the preset level;
        wherein the proximity sensor is activated when the mobile terminal is in the call mode.

2. The mobile terminal of claim 1, wherein the pulse wave sensing unit comprises:
    a signal processor configured to perform a signal processing of the pulse wave signal from the plurality of electrodes, and to provide the processed pulse wave signal to the controller; and
    a switch configured to control transmission of the pulse wave signal from the plurality of electrodes to the signal processor based on the control signal.

3. The mobile terminal of claim 2, wherein the proximity sensor provides the control signal to transfer the pulse wave signal to the signal processor, when an object is detected approaching a body of the mobile terminal.

4. The mobile terminal of claim 2, wherein the proximity sensor provides the control signal to transfer the pulse wave signal to the signal processor, when an object is detected approaching a body of the mobile terminal while the mobile terminal is in the call mode.

5. The mobile terminal of claim 1, wherein the plurality of electrodes includes a first electrode disposed at a front surface of a body of the mobile terminal and a second electrode disposed at a side surface of the body of the mobile terminal.

6. The mobile terminal of claim 1, wherein the controller is further configured to control the pulse wave sensing unit to transfer the pulse wave signal to the controller, when the mobile terminal is in the call mode.

7. The mobile terminal of claim 6, further comprising an interface unit configured to receive an earphone that includes the plurality of electrodes,
    wherein the controller controls the pulse wave sensing unit to transfer the pulse wave signal obtained via the plurality of electrodes of the earphone to the controller, when the mobile terminal is in the call mode and the earphone is coupled to the mobile terminal.

8. The mobile terminal of claim 1, wherein the controller is further configured to transmit a guide sound or a message for warning that the user is in an excited state to another party, when the determined excitement is equal to or greater than the preset level.

9. The mobile terminal of claim 1, wherein the controller is further configured to output at least one of a guide sound, a vibration sound, or a message for warning that the user is in an excited state, when the determined excitement is equal to or greater than the preset level.

10. The mobile terminal of claim 1, wherein the pulse wave signal is a bioelectric signal.

11. A method for measuring a bioelectric signal of a mobile terminal, the method comprising:
    determining that the mobile terminal enters a call mode and an object is detected through a proximity sensor;
    providing a control signal, for activating a pulse wave sensing unit, to the pulse wave sensing unit when the mobile terminal enters a call mode and the object is detected through the proximity sensor;

controlling the pulse wave sensing unit to obtain the pulse wave signal when the pulse wave sensing unit receives the control signal;

receiving a pulse wave signal from a plurality of electrodes that contact a user's skin surface when the pulse wave sensing unit receives the control signal;

acquiring at least one of a pulse wave data, a heart rate, and a heartbeat cycle based on the pulse wave signal;

determining whether a user's health state is abnormal considering that the acquired at least one of the pulse wave data, the heart rate, and the heartbeat cycle is deviated from a preset reference;

outputting a notification for warning abnormality of the user's health state through the mobile terminal and transmitting the notification to a call party, when the user's health state is abnormal;

transmitting the user's health state to a preset another party using a phone number and an e-mail address of the preset another party when a preset cycler arrives, storing position information of the mobile terminal and the user's health state coupled to the position information;

recommending or providing contents of a specific kind of help for the user's stability or relaxation, when the user's health state is determined to be abnormal and the call mode is terminated;

recommending specific restaurant position information related to a stored good health state of the user when the call mode is terminated and an application for searching restaurant position information is executed;

determining excitement information of the user based on the received pulse wave signal;

outputting an alarm when the determined excitement information is equal to or greater than a preset level; and terminating the call mode when the determined excitement information is equal to or greater than the preset level;

wherein the proximity sensor is activated when the mobile terminal is in the call mode.

12. The method of claim 11, further comprising determining a health state of the user based on the received pulse wave signal.

\* \* \* \* \*